United States Patent [19]

Lee, Jr. et al.

[11] 4,104,333

[45] Aug. 1, 1978

[54] SELF-CURING ARTIFICIAL FINGERNAILS

[75] Inventors: Henry L. Lee, Jr., Pasadena; Jan A. Orlowski, Altadena, both of Calif.

[73] Assignee: Lee Pharmaceuticals, South El Monte, Calif.

[21] Appl. No.: 855,629

[22] Filed: Nov. 29, 1977

Related U.S. Application Data

[63] Continuation of Ser. No. 665,214, Mar. 9, 1976, abandoned, which is a continuation of Ser. No. 527,221, Nov. 26, 1974, abandoned.

[51] Int. Cl.$^2$ ............................................. C08F 265/06
[52] U.S. Cl. .............................. 260/885; 260/31.8 M; 260/42.52; 424/61
[58] Field of Search ......................... 260/885; 424/61

[56] References Cited

U.S. PATENT DOCUMENTS

| | | | |
|---|---|---|---|
| 3,539,533 | 11/1970 | Lee | 260/47 |
| 3,632,677 | 1/1972 | Petner | 260/878 R |
| 3,647,498 | 3/1972 | Dougherty | 260/885 |

*Primary Examiner*—Paul R. Michl

[57] ABSTRACT

Self-curing artificial fingernail compositions containing crosslinking monomers, monoacrylates and suitable initiators and accelerators, and methods of polymerizing and applying same.

13 Claims, No Drawings

SELF-CURING ARTIFICIAL FINGERNAILS

This application is a continuation of our earlier patent application Ser. No. 665,214, filed Mar. 9, 1976, now abandoned, which in turn was a continuation of our earlier patent application, now abandoned, Ser. No. 527,221, filed Nov. 26, 1974.

BACKGROUND

While the advent of artifical fingernails was greeted with exceptional enthusiasm, complications since experienced have significantly dampened the enthusiasm. The most popular and widely-used artifical fingernail compositions have been two-part (liquid/powder) formulations wherein the liquid portion usually consists of methyl methacrylate monomer and a small amount of a polymerization accelerator or promoter, such as a tertiary amine, and the powder portion generally consists of polymethyl methacrylate and a catalyst, such as benzoyl peroxide.

In situ polymerization is effected by mixing a small amount of the liquid portion with a small amount of the powder portion on the end of a brush, and the mixture brushed on the nail surface to be repaired, protected or elongated. Elongation requires affixing a substrate means to the exposed edge of the nail, which means has the general contour of the natural nail and extends therefrom to the desired length and along the plane of the natural nail. The substrate is preferably of a material to which the polymerized mixture does not adhere. In this way it may be removed following construction of the artificial nail.

Blending the powder/liquid portions, as by brushing, results in at least a part of the powder dissolving in the liquid monomer, and the monomer polymerizes simultaneously through the action of the accelerator and catalyst. The mixing and brushing steps are repeated as often as needed to form the desired thickness and nail form. When polymerization is completed, the artificial nail may then be smoothed, shaped and a nail polish applied if desired.

As is well known, natural nails (fingernails and toenails) are afflicted with may problems related to health, accidents and abuse. For example, various genetic and disease-related abnormalities may disrupt nail growth, texture, thickness and strength, thus promoting fingertip injury and unsightliness. Accidents occur to produce nail damage, such as tearing, splitting, breaking and scarring. Likewise, nails are abused by so-called "nailbiters". There being no real medical solutions to these problems, the advent of artificial fingernails of the aforementioned type was a most welcome development.

Unfortunately, however, the fingernail preparations just described are not without serious inherent drawbacks and disadvantages. Important among these disadvantages is the fact that the principal constituent of the liquid portion, methyl methacrylate, is a low molecular weight, volatile compound with a penetrating, unpleasant odor. In fact, methyl methacrylate monomer has been shown to cause severe dermatologcal reactions, cardiovascular irregularities and other ailments. Although the prepolymerized powder appears safe in these formulations, the polymerization of monomer which proceeds in situ after mixing powder and liquid is far from complete, because of the nature of the reactant. Consequently, unreacted methyl methacrylate is available to cause dermatitis and other ailments.

Another disadvantage present formulations have is that the presence of unreacted low molecular weight methyl methacrylate in the matrix of the resulting polymer structure weakens same and generally leads not only to an artificial fingernail polymer of low mechanical strength, brittleness and lack of flexibility, but also leads to a lack of reproducibility of properties due to variations in the completeness of polymerization.

Another disadvantage of present formulations rests in the fact that they produce a high exotherm during polymerization, in some cases requiring that fingers be cooled in water following application.

A further disadvantage of present formulations is the time-consuming nature of the applicaton process, which in part is a result of poor application qualities of the material, and in part a result of excessive time needed in finishing the nail because of the poor mechanical quality of the artificial nail.

It follows from the above-noted multiple disadvantages that there is a definite need for artificial nails which can be applied with greater safety and which exhibit greater strength, greater impact resistance, greater flexibility, greater processability, greater reproducibility, and lower exotherm during polymerization. The present invention not only fills this need but further provides even better wear resistance, retention, resistance to chemical solutions and moisture. In short, the compositions of instant discovery at once obviate the serious drawbacks hereinbefore discussed and provide superior physical, mechanical and cosmetic properties. As such, they are directed to the "cosmeticulous".

The following references, of varying degrees of relevance, were uncovered in a recent study of the artificial fingernail art: U.S. Pat. Nos. 2,073,867, H. A. Feigenbaum; 2,688,331, B. Bogoslowsky; 2,941,535, R. J. Lappe; 2,979,061, J. Greenman et al; 2,633,139, H. L. Pettey; 3,037,514, M. M. Lappe; 3,157,912, D. Lisczawka; 3,425,426, F. P. Welanetz; 3,478,576, Sautter et al; 3,483,289, J. B. Michaelson; 3,487,831, M. Jaume et al; 3,502,088, S. Jarby; 3,553,401, J. M. Michaelson; 3,574,822, Thomas H. Shepherd et al; 3,645,835, M. E. Hodgson; Chemical Abstracts, Vol. 61, page 1704(f) Cosmetics, Science and Technology, September 16, 1957, pages 693–716.

INVENTION

The present invention concerns artificial nail compositions comprising, by weight, (a) from about 5% to about 80%, preferably about 10% to about 80%, of an aromatic, cycloaliphatic or aliphatic crosslinking monomer containing at least two groups able to polymerize in the presence of a peroxide-type initiator (catalyst) and a tertiary amine-type accelerator (promoter), (b) from 0 to about 60%, preferably less than about 45%, of a monoacrylate monomer, (c) a peroxide-type initiator, and (d) a tertiary amine-type accelerator. More particularly, the instant discovery relates to artificial nail compositions, of the type and in the concentrations just described, in which the initiator, such as benzoyl peroxide, is present in the concentration of about 0.2% to about 4.0%, by weight, and the accelerator, such as N,N-dimethyl-p-toluidine, is present in the concentration of about 0.1% to about 8.0% by weight. Generally, but not necessarily, a polymeric filler, such as a polyacrylate, is present in the composition, as will be seen hereinafter.

Among the crosslinking monomers herein contemplated are 2,2bis[4'(-3''-methacryloyl-2''-hydroxypropoxy)phenyl] propane, mono-, di-, tri-, tetra-, and polyethylene glycol dimethacrylates; diallyl fumarate, 2,2bis (4'-methacryloyl phenyl) propane, 2,2 bis (4'-methacryloylethyloxyphenyl) propane, diallyphthalate, butene-diol-1,4-dimethacrylate, allylmethacrylate, bis(2-methacryloylethyl) o-, m-, and p- phthalates, 2-acryloylethylmethacrylate.

Other similar crosslinking monomers having at least two groups or moieties, such as allyl, acryloyl, methacryloyl or other similar unsaturations, capable of polymerizing in the presence of the initiators and accelerators of the present invention are herein contemplated. Typically, these monomers are not only mono-polymerizable, so to speak, and co-polymerizable but they are suitable crosslinking agents for acrylic polymers.

Typical monoacrylates (acrylic and methacrylic esters) within the purview of the present invention are (1) substituted or unsubstituted, lower alkyl or alkenyl ($C_1-C_5$) and cycloalkyl methacrylates, including but not limited to methyl methacrylate, ethyl methacrylate, propyl methacrylate, butyl methacrylate, hydroxyethyl methacrylate, glycidyl methacrylate, cyclohexyl methacrylate and cyclopentyl methacrylate, tetrahydrofurfurylmethacrylate, and (2) substituted or unsubstituted, lower alkyl or alkenyl ($C_1-C_5$) and cycloalky acrylates, including but not limited to methyl acrylate, ethyl acrylate, propyl acrylate, butyl acrylate, hydroxyethyl acrylate, glycidyl acrylate, tetrahydrofurfurylacrylate, cyclopentyl acrylate and cyclohexyl acrylate. Obviously, substitutent moieties other than hydroxy and epoxy which do not interfere with or significantly disrupt the intended polymerization reaction are herein contemplated.

As suggested hereinabove, it has been found pursuant to the instant discovery that, quite surprisingly, the superior results hereinbefore described may be achieved and the likewise heretofore-mentioned drawbacks may be avoided using the crosslinking monomers alone or in admixture, as taught supra, with the monoacrylates. For best results, when combining the crosslinking monomers with the monoacrylates, the former are present in a concentration of at least 5% of the weight concentration of monoacrylate or monoacrylates. Of course, blends of crosslinking monomers and blends of monoacrylates may be employed if desired.

Of the initiators herein contemplated, the preferred are the free-radical catalysts, such as the organic peroxides and particularly benzoyl peroxide and lauroyl peroxide.

The accelerators within the purview of the instant discovery and preferred are the tertiary amines, especially N,N-di(lower)alkyl-p-toluidines (e.g., N,N-dimethyl-p-toluidine, N,N-diethyl-p-toluidine) and N,N-di (lower) alkyl anilines, such as N,N-dimethyl aniline.

Of course, other conventional free-radical catalysts and promoters, while not at present preferred, may be used in lieu of or in conjunction with (when compatible) the foregoing.

The set time for the compositions of the present invention, usually about 120 to about 400 seconds, may be regulated by varying the concnetration of initiators and/or accelerators. Inorganic fillers, such as finely-divided alumina silicates, silica, quartz, glass, and the like, may be used to control consistency of material and improve its physical and mechanical properties.

Generally, as suggested hereinbefore, a polymeric filler material which may be soluble, partially soluble or insoluble in the resin matrix is present. Typically, but not necessarily, these are polymers or copolymers of the monomeric materials used in the in situ polymerization composition. Suitable for and very effective in the compositions of the present invention are copolymeris of ethyl and methyl methacrylate, polyethyl methacrylate, polymethyl methacrylate, polymethyl acrylate, polyethyl acrylate and polypropyl acrylate. In other words, polymers of the monoacrylates herein contemplated are suitable.

The just-mentioned fillers are usually present in a concentration of less than about 60%, preferably from about 5% to about 55%, by weight.

Minor conventional amounts of modifiers may also be present, such as dyes, opaquing agents (e.g., titanium dioxide), and stabilizers (e.g., 3-butyl-4-hydroxytoluene).

According to another embodiment of the present invention, it has been found that the flexibility of the aforementioned cured fingernail compositions is significantly enhanced by incorporationg in the precursor polymerizable composition from about 2 to about 20%, by weight, of esters of aromatic compounds, such as mono-, di-, tri- and poly- ethylene glycol dibenzoates, lower alkyl ($C_1-C_5$) phthalates or diphthalates, and cycloalkylphthalates or cycloalkyldiphthalates, e.g., cyclopentylphthalate, cyclohexylphthalate, cyclopentyldiphthalate, and cyclohexyldiphthalate.

The concentrations given herein are based upon the combined wiehgt (100%) of all of the components which are blended to make up the final composition. Of course, it is appreciated that in situ polymerization is preferably carried out by blending two-part formulations (e.g., liquid/powder portions). Upon blending both formulations, the resulting mixture contains the individual components in concentrations within the ranges hereinabove recited. For convenience, however, the weight concentration of each component in each of the examples, infra, is recited as a percentage of the individual formulation, i.e., part A or part B.

The ratio of the parts, i.e., the ratio of part A to part B, may vary from about 3:1 to about 1:3, depending upon the application properties desired, so long as the component concentrations in the resulting mixture are within the range herein recited. The 3:1 to 1:3 combination mixes well, flows well and gives a satisfactory degree of color and translucency for most nails. It cures reliably, with a reproducible set time and superior and reproducible physical and mechanical properties. On the basis of dermatological testing performed on a number of women, the compositions herein contemplated have acceptable properties.

EXAMPLES

The present invention will be more fully described by reference to the following examples which illustrate certain preferred embodiments of the present invention.

EXAMPLES I

| | Percent by Weight |
|---|---|
| Part A (Powder) | |
| 70/30 copolymer of ethyl and methyl methacrylate | 99.1 |
| benzoyl peroxide (catalyst) | 0.8 |
| titanium dioxide (opaquing agent) | 0.1 |

-continued

| Part B (Liquid) | Percent by Weight |
|---|---|
| methyl methacrylate | 78.35 |
| polyethylene glycol dimethacrylate | 20.0 |
| dimethyl-p-toluidine (accelerator) | 1.0 |
| 2-hydroxy-4-methoxy benzophenone (UV-absorber) | 0.5 |
| 3-butyl-4-hydroxy toluene (stabilizer) | 0.05 |
| dye | 0.1 |

Typical physical properties of the cured composition are as follows:

| Hardness, Shore D | 88 |
|---|---|
| Compressive strength, psi | 10,600 |
| Flexural strength, psi | 10,700 |
| Flexural modulus, psi | 16,000 |

In this example and in the examples which follow, both parts (be they liquid/powder or paste/paste) are applied separately and mixed on the nail. Of course, it can be appreciated that alternatively both parts may be pre-mixed immediately before application on the nail or substrate elongator.

In Examples I–V the ratio of A to B, as applied is 1:1.

EXAMPLE II

| | Percent by Weight |
|---|---|
| Part A (Powder) | |
| 70/30 copolymer of ethyl and methyl methacrylate | 50.4 |
| polymethyl methacrylate | 48.4 |
| benzoyl peroxide (catalyst) | 1.0 |
| titanium dioxide (opaquing agent) | 0.2 |
| Part B (Liquid) | |
| methyl methacrylate | 60.0 |
| cyclohexyl methacrylate | 15.5 |
| triethylene glycol dimethacrylate | 22.85 |
| dimethyl-p-toluidine (accelerator) | 1.0 |
| 2-hydroxy-4-methoxy-benzophenone (UV-absorber) | 0.5 |
| 3-butyl-4-hydroxytoluene (stabilizer) | 0.05 |
| dye | 0.1 |

EXAMPLE III

| | Percent by Weight |
|---|---|
| Part A (Powder) | |
| polymethyl methacrylate | 98.7 |
| benzoyl peroxide (catalyst) | 1.0 |
| titanium dioxide (opaquing agent) | 0.3 |
| Part B (Liquid) | |
| methyl methacrylate | 30.5 |
| ethyl methacrylate | 35.0 |
| allyl methacrylate | 5.0 |
| BIS/GMA* | 3.0 |
| 50-50 mixture of di- and tri-ethylene glycol dimethacrylates | 23.9 |
| N-bis (2-hydroxyethyl)-p-toluidine (accelerator) | 2.0 |
| 2-hydroxy-4-methoxy-benzophenone (UV absorber) | 0.5 |
| 3-butyl-4-hydroxy toluene (stabilizer) | 0.1 |

*2,2 bis[4'(-3"-methacryloyl-2"-hydroxypropoxy)phenyl]propane

EXAMPLE IV

It has been found possible, as illustrated in this example, to formulate these ingredients as a two-paste system rather than a powder-liquid system. The same superior qualities are realized in the two-paste system as in the powder-liquid system. In addition, application is faster and smoother. The two pastes are preferably mixed in a ratio of 1:1.

| | Percent by Weight |
|---|---|
| Part A (Paste) | |
| ethyl methacrylate | 50.9 |
| polyethylene glycol dimethacrylate | 10.7 |
| triethylene glycol dibenzoate | 7.0 |
| sub-micron synthetic crystalline silica | 21.1 |
| N,N-dimethyl-p-toluidine (accelerator) | 1.1 |
| 3-butyl-4-hydroxytoluene | 0.19 |
| dye | 0.01 |
| Part B (Paste) | |
| ethyl methacrylate | 59.2 |
| polyethylene glycol dimethacrylate | 10.5 |
| triethylene glycol dibenzoate | 7.0 |
| sub-micron synthetic crystalline silica | 21.0 |
| 3-butyl-4-hydroxytoluene (stabilizer) | 0.2 |
| benzoyl peroxide (catalyst) | 2.1 |

EXAMPLE V

| | Percent by Weight |
|---|---|
| Part A (Powder) | |
| 70/30 copolymer of ethyl and methyl methacrylate | 99.1 |
| benzoyl peroxide (catalyst) | 0.8 |
| titanium dioxide (opaquer) | 0.1 |
| Part B (Liquid) | |
| 2-hydroxyethyl methacrylate | 72.1 |
| polyethylene glycol dimethacrylate | 21.25 |
| triethylene glycol dibenzoate | 5.0 |
| N,N-dimethyl-p-toluidine (accelerator) | 1.0 |
| 2-hydroxy-4-methoxy-benzophenone (UV-absorber) | 0.5 |
| 3-butyl-4-hydroxytoluene (stabilizer) | 0.05 |
| dye | 0.1 |

Typical physical properties of the cured polymer are as follows:

| Hardness, Shore D | 86 |
|---|---|
| Compressive strength, psi | 13,000 |
| Flexural strength, psi | 7,200 |
| Flexural modulus, psi | 14,000 |

As indicated hereinabove, in Examples I–V the ratio of A to B, as applied, is 1:1.

EXAMPLE VI

| | Percent by Weight |
|---|---|
| Part A (Powder) | |
| polymethyl methacrylate | 90.0 |
| colloidal silica | 9.1 |
| benzoyl peroxide (catalyst) | 0.9 |
| Part B (Liquid) | |
| polyethyleneglycoldimethylacrylate | 98.3 |
| N,N-dimethyl-p-toluidine | 1.0 |
| 2-hydroxy-4-methoxybenzophenone (UV absorber) | 0.5 |
| 3-butyl-4-hydroxytoluene (stabilizer) | 0.1 |
| dye | 0.1 |

In Example VI the ratio of A to B, as applied according to Example I, is 2:1.

EXAMPLE VII

| Part A (Powder) | Percent by Weight |
| --- | --- |
| 70/30 copolymer of ethyl methylmethacrylate | 80.0 |
| polymethylmethacrylate | 19.0 |
| benzoyl peroxide (catalyst) | 0.9 |
| titanium dioxide (opaquer) | 0.1 |
| Part B (Liquid) | |
| tetrahydrofurfurylmethacrylate | 85.9 |
| diallyphthalate | 5.0 |
| diethylene glycol dimethacrylate | 8.0 |
| N,N-dimethyl-p-toluidine | 1.0 |
| hydroquinone (stabilizer) | 0.05 |
| dye | 0.05 |

In Example VII the ratio of A to B, as applied according to Example I, is 1:3.

EXAMPLE VIII

| Part A (Powder) | Percent by Weight |
| --- | --- |
| 70/30 copolymer of ethyl and methyl methacrylate | 50.4 |
| polymethyl methacrylate | 48.4 |
| benzoyl peroxide (catalyst) | 1.0 |
| titanium dioxide (opaquing agent) | 0.2 |
| Part B (Liquid) | |
| tetrahydrofurfurylmethacrylate | 88.35 |
| diethylene glycol dimethacrylate | 10.00 |
| N,N bis(2-hydroxyethyl)-p-toluidine | 1.0 |
| 2-hydroxy-4-methoxy-benzophenone (UV absorber) | 0.5 |
| 3-butyl-4-hydroxytoluene (stabilizer) | 0.05 |
| dye | 0.1 |

In Example VIII the ratio of A to B, as applied according to Example I, is 1:1.

Pursuant to statuatory requirements there are described above the invention and what are now considered its best embodiments. It should be understood, however, that the invention can be practiced otherwise than as specifically described, within the scope of the appended claims.

What is claimed is:

1. A self-curing, dermatologically acceptable composition to be applied to a natural nail as a hardenable coating or to form an artificial nail, which composition consists essentially of a mixture of the following ingredients, by weight based on the total weight of the composition:
   (a) from about 5% to about 80% of a first addition polymerizable, ethylenically unsaturated monomer that can form a cross-linked polymer upon polymerization during self-curing of the composition, which monomer contains in its molecule at least two groups that are capable of being addition polymerized upon contact with a peroxide-type free radical initiator and a tertiary amine-type accelerator, the polymerizable groups being members of the group consisting of allyl, acryloyl, methacryloyl, or combinations thereof;
   (b) a second monomer that is monoethylenically unsaturated, in an amount up to about 60%, that copolymerizes with the first monomer upon self-curing of the composition to form a copolymeric structure that is cross-linked, the second monomer being either tetrahydrofurfuryl acrylate or tetrahydrofurfuryl methacrylate;
   (c) a peroxide-type free radical initiator;
   (d) a tertiary amine-type accelerator; and
   (e) from about 5% to about 60% of a polymeric filler that is at least partially soluble in the composition; the composition being formulated and the initiator and the accelerator being present in a quantity to cause self-curing to occur in situ within about 120 to about 400 seconds after mixture of the ingredients and application to a nail, under ambient conditions to which the nail is normally exposed including ambient temperature and the presence of atmospheric oxygen.

2. A composition in accordance with claim 1 wherein the second monomer is present in a minor amount, less than 45% by weight of the composition.

3. A composition in accordance with claim 2 wherein the initiator is present in an amount in the range from about 0.2% to about 4%, and the accelerator is present in an amount from about 0.1% to about 8%, the percentages being by weight of the composition.

4. A composition in accordance with claim 3 wherein the polymeric filler is soluble in the composition and is present in an amount from about 5% to about 55% by weight of the composition.

5. A composition in accordance with claim 4 including from about 2% to about 20% by weight of the composition of an aromatic ester as a flexibilizing material.

6. A composition in accordance with claim 1 wherein the (a) monomer is selected from the group consisting of 2,2 bis [4'(3'-methacryloyl-2''-hydroxypropoxy)-phenyl]propane; mono-, di-, tri-, tetra-, and polyethylene glycol dimethacrylates; diallyl fumarate; 2,2 bis (4'-methacryloyl phenyl) propane; 2,2 bis (4'-methacryloylethyloxy-phenyl) propane; diallyl phthalate; butenediol-1,4,-dimethacrylate; allyl methacrylate; bis (2-methacryloylethyl) o-, m-, and p-phthalates; 2-acryloylethylmethacrylates, and mixtures thereof.

7. A composition in accordance with claim 3 wherein the (a) monomer is polyethylene glycol dimethacrylate.

8. A composition in accordance with claim 5 wherein the (a) monomer is triethylene glycol dimethacrylate.

9. A composition in accordance with claim 5 wherein the (a) monomer is a mixture of allyl methacrylate; bis-GMA, and a mixture of diethylene glycol and triethylene glycol dimethacrylates.

10. A composition in accordance with claim 5 wherein the (a) monomer is a mixture of diallyl phthalate and diethylene glycol dimethacrylate.

11. A composition in accordance with claim 5 wherein the (a) monomer is diethylene glycol dimethacrylate.

12. A self-curing, dermatologically acceptable composition to be applied to a natural nail as a hardenable coating or to form an artificial nail, which composition consists essentially of a mixture of the following ingredients, by weight based on the total weight of the composition:
   (a) from about 5% to about 80% of a first addition polymerizable, ethylenically unsaturated cross-linkable monomer selected from the group consisting of 2,2bis [4'(3''-methacryloyl-2''-hydroxypropoxy) phenyl] propane; mono-, di-, tri-, tetra-, and polyethylene glycol dimethacrylates; diallyl fumarate; 2,2 bis (4'-methacryloyl phenyl) propane; 2,2 bis (4'-methacryloylethyloxy-phenyl) propane; diallyl phthalate, butenediol-1, 4-dimethacrylate; allyl methacrylate, bis(2-methacryloylethyl) o-, m-, and p-phthalates; 2-acryloylethylmethacrylates; and mixtures thereof;

(b) a second monomer that is monoethylenically unsaturated, in an amount to about 45%, that copolymerizes with the first monomer upon self-curing of the composition to form a copolymeric structure that is cross-linked, said second monomer being either tetrahydrofurfuryl acrylate or tetrahydrofurfuryl methacrylate;

(c) from about 0.2% to about 4.0% of a peroxide-type free radical initiator;

(d) from about 0.1% to about 8.0% of a tertiary amine-type accelerator;

(e) from about 5% to about 55% of a polymeric filler that is at least partially soluble in the composition; and (f) from about 2% to about 20% of an aromatic ester as a flexibilizing material;

the composition being formulated and the initiator and accelerator being present in a quantity to cause self-curing to occur in situ without about 120 to about 400 seconds after mixing the ingredients and application to a nail, under ambient conditions to which the nail is normally exposed including ambient temperature and the presence of atmospheric oxygen.

13. A composition suitable to be applied to a fingernail as a hardenable coating or to form an artificial nail, which composition consists essentially of a mixture of the following ingredients, by weight based on the total weight of the composition;

(a) from about 5% to about 80% of a cross-linkable monomer selected from the group consisting of ethylene glycol dimethacrylate, diethylene glycol dimethacrylate, triethylene glycol dimethacrylate, polyethylene glycol dimethacrylate, and mixtures thereof, that are capable of being polymerized upon contact with a peroxide-type free radical initiator and a tertiary amine-type accelerator;

(b) a minor amount up to about 45% of tetrahydrofurfuryl methacrylate, (c) from about 0.2% to about 4.0% of benzoyl peroxide;

(d) from about 0.1% to about 8.0% of a tertiary amine-type accelerator;

(e) from about 5% to about 55% of a polymeric filler that is at least partially soluble in the composition; and (f) from about 2% to about 20% of a flexibilizing material;

the initiator and the accelerator being present in a quantity to cause curing to occur within about 120 to about 400 seconds after mixing the ingredients, under ambient conditions to which the nail is normally exposed including ambient temperature and the presence of atmospheric oxygen.

* * * * *